United States Patent [19]

Hill et al.

[11] Patent Number: 5,453,510
[45] Date of Patent: Sep. 26, 1995

[54] NEUROMUSCULAR BLOCKING AGENTS

[75] Inventors: Derek A. Hill; Geoffrey L. Turner, both of Dartford, England

[73] Assignee: Burroughs Wellcome Co., Research Triangle Park, N.C.

[21] Appl. No.: 911,887

[22] Filed: Jul. 10, 1992

Related U.S. Application Data

[63] Continuation-in-part of Ser. No. 729,496, Jul. 12, 1991, abandoned.

Foreign Application Priority Data

Jul. 13, 1990 [GB] United Kingdom .................. 9015473

[51] Int. Cl.$^6$ ........................ A61K 31/47; C07D 217/24
[52] U.S. Cl. ................................................................ 546/140
[58] Field of Search ........................... 546/140; 514/308

[56] References Cited

U.S. PATENT DOCUMENTS

| | | | |
|---|---|---|---|
| 3,004,031 | 10/1961 | Taylor et al. | 546/140 |
| 4,179,507 | 12/1979 | Stenloke et al. | 546/140 |
| 4,192,877 | 3/1980 | Savarese et al. | 546/140 |
| 4,578,467 | 3/1986 | Bonacchi | 544/360 |
| 4,761,418 | 8/1988 | Swaringer, Jr. et al. | 546/140 |

OTHER PUBLICATIONS

Knabe, "Chirale Wirksubstanzen", Deutche Apatheken Seitung, 116 Jahrg, No. 24, pp. 849–851, 1989.
Nehmer, "Jour. of Chromatography" vol. 457, 1988, pp. 127–135.

*Primary Examiner*—C. Warren Ivy
*Assistant Examiner*—D. Margaret M. Mach
*Attorney, Agent, or Firm*—Donald Brown; Lawrence A. Nielsen

[57] ABSTRACT

1R-cis,1'R-cis isomer of a 2',2'-(3,11-dioxo-4,10-dioxatridecylene)-bis(1,2,3,4-tetrahydro-6, 7-dimethoxy-2-methyl-1-veratrylisoquinolium) said, substantially free from other geometrical and optical isomers thereof. The 1R-cis,1'R-cis isomer has been found to have an advantageous combination of pharmacological properties, notably greater neuromuscular blocking potency, weaker histamine-releasing potency, and at equivalent levels of neuromuscular blockade, fewer potential adverse effects on the autonomic nervous system (sympathetic and parasympathetic blockage), in comparison with the known mixture of geometrical and optical isomers.

24 Claims, No Drawings

NEUROMUSCULAR BLOCKING AGENTS

This application is a continuation in part of U.S. Ser. No. 07/729,496 filed Jul. 12, 1991 now abandoned.

The present invention relates to an isoquinoline compound useful as a neuromuscular blocking agent.

Neuromuscular blocking agents are widely used in surgical anaesthesia to relax the skeletal muscles to aid the work of the surgeon. Such agents are also widely used in Intensive Care Units (ICU) of hospitals to provide long-term muscle relaxation in patients who have been intubated to provide controlled ventilation of the patient.

Atracurium besylate (i.e. 2,2'-(3,11-dioxo-4,10-dioxatridecylene)-bis-( 1,2,3,4-tetrahydro-6,7-dimethoxy-2-methyl-1-veratrylisoquinolium dibesylate) is a non-depolarizing neuromuscular blocking agent which first became available for human surgical use in the UK in December 1982 and a year later in the USA. The compound is described in UK Patent Specification No. 1579822 and U.S. Pat. No. 4,179,507. The drug is now widely used in surgery and ICU therapy. The drug was designed uniquely to undergo spontaneous degradation by "Hofmann" elimination at physiological pH and temperature and by an ester hydrolysis which proceeds independently of hepatic and renal function. For human surgical use, atracurium besylate is employed as a mixture of ten optical and geometrical isomers. Eur. J. Med. Chem-Chem, Ther. 1984-19, No. 5, pages 441–450 refer to the geometrical and optical isomers of atracurium besylate.

Hplc separation methods for atracurium published up to the filling date of U.S. Ser. No. 07/729,496 used aqueous mobile phases. We have found that aqueous mobile phases do not allow the recovery of the isomers of atracurium without substantial degradation of the product. It has been discovered that the use of a non-aqueous mobile phase allows isolation of a 1R-cis, 1'R-cis atracurium salt substantially free of degradation products and other atracurium isomers.

Neuromuscular blocking agents such as atracurium besylate act by blocking the receptor for acetylcholine at the neuromuscular junction. However, they may also block cholinergic transmission in the autonomic nervous system and produce unwanted cardiovascular side effects. For example, parasympathetic blockade results in tachycardia and hypertension whereas blockade of sympathetic ganglia will cause bradycardia and hypotension. Neuromuscular blocking agents also have the propensity of releasing histamine which can produce life-threatening anaphylactoid reactions in some patients. The antigenic group in skeletal muscle relaxant drugs is the quaternary or tertiary ammonium structure which also confers the neuromuscular blocking properties upon these agents. In this respect atracurium in a weak histamine liberator and, as with other neuromuscular blocking agents, there have been occasional reports of anaphylactoid reactions attributed to the drug.

We have now discovered that atracurium salts in which the atracurium moiety has a particular geometrical and optical isomeric configuration have an especially advantageous combination of pharmacological properties that render such salts of exceptional benefit as neuromuscular blocking agents.

The particular geometrical and optical isomeric configuration for the atracurium moiety referred to above is the 1R-cis,1'R-cis configuration. Atracurium salts having this configuration can be named as 1R-cis,1'R-cis-2',2'-(3,11-dioxo-4,10-dioxatridecylene)-bis-( 1,2,3,4-tetrahydro-6,7-dimethoxy-2-methoxyl-1-veratrylisoquinolinium) salts. Such salts will be referred to as hereinafter as 1R-cis,1'R-cis atracurium salts.

According to one feature of the present invention we provide a 1R-cis, 1'R-cis atracurium salt substantially free from other geometrical and optical isomers thereof.

The 1R-cis,1'R-cis atracurium salt according to the invention are in admixture with less than 8% w/w of other geometrical and optical isomers most suitably less than 5% w/w, and preferably less than 2% w/w of such other isomers, based on the total weight of the relevant mixture. In particular, the above 1R-cis, 1'R-cis salts according to the invention advantageously contain (a) less than 1% w/w of the corresponding cis, trans isomers and/or less than 0.5% w/w of the trans, trans isomers and/or (b) generally less than 5% w/w, preferably less than 2% w/w of the corresponding S-isomers.

For human administration, e.g. for use in surgery or medical therapy, e.g. in anaesthesia, the 1R-cis,1'R-cis atracurium salts according to the invention will include a physiologically acceptable anion, preferred anions including the halide, eg chloride, bromide or iodide, sulphate, phosphate, hydrogen phosphate, acetate, propionate, succinate, maleate and organosulphonate, eg methanesulphonate (mesylate), benzenesulphonate (besylate), p-toluenesulphonate (tosylate) and naphthalenesulphonate anions, the mesylate and besylate anions being especially preferred. Such salts containing a physiologically acceptable anion will be referred to hereinafter as physiologically acceptable 1R-cis-1'R-cis atracurium salts.

Atracurium salts including a non-physiologically acceptable anion may be employed in the synthesis of a corresponding physiologically acceptable salt.

With regard to the especially advantageous combination of pharmacological properties referred to above, we have discovered from experiments in animals that the 1R-cis,1'R-cis atracurium salts have a significantly greater neuromuscular blocking potency than atracurium besylate in the form of a mixture of geometrical and optical isomers while having a similar duration of action.

The 1R-cis-1'R-cis atracurium salts also exhibit a lower level of potential adverse effects on the autonomic nervous system including sympathetic blockade and parasympathetic blockade, and with less likelihood of producing histamine-like cardiovascular effects at therapeutic dosages, thereby providing a greater measure of patient safety, in comparison with atracurium besylate in the form of a mixture of geometrical and optical isomers. Histamine-like cardiovascular effects result in a decrease in blood pressure and an increase in heart rate.

A further advantage of the 1R-cis,1'R-cis, atracurium salts according to the invention is that they provide a more efficient neuromuscular blockade with the formation of lower levels of degradation products than the above-mentioned mixture of atracurium besylate isomers. This advantage is particularly desirable for longer surgical procedures and for ICV use involving high doses and/or long periods of treatment.

The degradation products of atracurium comprise of four major products namely:

Laudanosine
2-(2-carboxyethyl)1,2,3,4-tetrahydro-6,7,dimethoxy-2-methyl-1-veratrylisoquinolinium besylate
2-(5-hydroxypentyloxy carbonylethyl)-1,2,3,4-tetrahydro-6,7,dimethoxy- 2-methyl-1-veratrylisoquinolinium besylate 2-[2-(5-acryloxloxypentyloxycarbonyl)ethyl]1,2,3,4-tetrahydro-6,7,-dimethoxy- 2-methyl-1-veratrylisoquinolinium besylate The present invention further provides:

a) physiologically acceptable 1R-cis-1'R-cis atracurium salts according to the invention for use in surgery or medical therapy, e.g. in anaesthesia, particularly for inducing neuromuscular blockade in an animal, eg a mammal such as man;

b) the use of physiologically acceptable 1R,cis,1'R-cis atracurium salts according to the invention for the manufacture of a pharmaceutical formulation for inducing neuromuscular blockade; and c) a method of inducing neuromuscular blockade in an animal, eg a mammal such as man which comprises administering to said animal a neuromuscular blockade—effective amount of a physiologically acceptable 1R-cis,1'R-cis atracurium salt according to the invention.

The physiologically acceptable 1R-cis,1'R-cis atracurium salts according to the invention are generally employed in surgery or medical therapy, e.g. in anaesthesia, by administering the salts to the relevant subject, eg man, by an appropriate route and at an appropriate dosage to achieve the desired level of neuromuscular blockade. The salts are generally administered by injection by the intravenous of intramuscular route, or, if required, by continuous intravenous infusion. The precise dosage at which the salts will be administered will vary depending on the degree of neuromuscular blockade required, the age and condition of the subject. However, when administered by the intravenous route, the salts are generally administered in a single injection at a dosage of 0.1 to 0.6 mg/kg body weight, preferably 0.2 to 0.4 mg/kg body weight. In the case of administration by infusion, the salts are generally employed in a dosage of 0.1 to 0.6 mg/kg body weight/hour, preferably 0.2 to 0.4 mg/kg body weight/hour.

The 1-R-cis,1'R-cis atracurium salts according to the invention are generally employed in surgery or medical therapy in the form of a pharmaceutical formulation comprising such a salt together with a pharmaceutically acceptable carrier therefor. Such formulations are preferably adapted for administration by injection or infusion, eg as a solution, emulsion or suspension of the salt in a pharmaceutically acceptable aqueous or non-aqueous liquid, for example sterile water which may additionally contain if desired one or more other appropriate excipients such as bacteriostatic agents, antioxidants, buffers, thickening agents, or suspending agents. Such liquid formulations generally contain the salt in an amount of 5 to 15, preferably 5 to 10 mg/ml. Alternatively, the salts may be presented as lyophilised solids for reconstitution with water for injection or with dextrose or saline solutions. The formulations according to the invention are generally presented in unit dosage forms such as ampoules or disposable injection devices or in multidose forms such as a bottle from which the appropriate dose may be withdrawn; all such formulations should be sterile. Such unit dosage forms generally contain 10 to 250 mg preferably 25 to 50 mg of a salt according to the invention in solution or as a lyophilised solid.

The 1R-cis,1'R-cis atracurium salts according to the invention may be prepared by subjecting the corresponding 1R,1'R atracurium salt to conditions or reagents serving to effect isolation of the 1R-cis, 1'R-cis isomer from the corresponding geometrical isomers contained in the said 1R,1'R atracurium salt.

Isolation of the desired 1R-cis,1'R-cis atracurium salt in accordance with the above process is effected by high performance liquid chromatography (hplc) using a column packed with silica and a non-aqueous mobile phase in the presence of a strong acid. The non-aqueous mobile phase comprises an appropriate mixture of solvents, e.g. a mixture of a chlorinated hydrocarbon such as methylene chloride, or acetonitrile; an alcohol e.g. a short-chain aliphatic alcohol such as methanol, ethanol or propanol; and suitable strong acids include benzenesulphonate acid, methanesulphonic acid, p-toluenesulphonic acid and phosphoric acid. A mixture of methylene chloride: methanol: methane sulphonic acid, preferably in a ratio of 80:20:0.5, has been found to be especially advantageous, resulting in elution of the methanesulphonate (mesylate) salt from the column. Similarly for elution of the benzenesulphonate (besylate) salt, a solvent mixture of methylene chloride; methanol: benzenesulphonic acid (4000:500:0.25) is preferred. The eluted salt solution may subsequently be washed to remove solvents such as methanol and any excess acid and isolated by evaporation of the chlorinated hydrocarbon. The desired salt may be obtained as a solid by lyophilisation of an aqueous solution of the salt or by dissolution in a solvent such as dichloromethane then precipitation by addition of a nonpolar solvent such as petroleum ether or cyclohexane.

The 1R, 1'R atracurium salt used as starting material in the above process may be prepared from (R)-1,2,3,4-tetrahydropapaverine in conventional manner, e.g. by the method described in Eur. J. Med. Chem.-Chim. Ther. 1984-19, N., 5, pages 445–450.

The following Examples illustrate the present invention:

EXAMPLE 1 a) 1,5-Pentamethylene diacrylate 1,5-Pentanediol (15.6 g) was heated in refluxing toluene (500 ml) with 3-bromopropionic acid (50.5 g) and a trace of p-toluenesulphonic acid for 4 hours. The cooled toluene solution was then washed with aqueous sodium acetate solution and treated with triethylamine (50 ml) at reflux. The cooled reaction mixture was washed well with water to remove triethylamine and triethylamine hydrobromide and then the toluene was removed under reduced pressure.

The product, 1,5-pentamethylene diacrylate (24.0 g, 75% yield) was obtained as a pale liquid by high vacuum distillation (b.p. 90°–95° C./0.1 mm Hg).

b) (R)-Tetrahydropapaverine (±)-Tetrahydropapaverine hydrochloride (105 g) was dissolved in water and the solution was made alkaline with dilute aqueous ammonia. The precipitated (±)-tetrahydropaverine base was dissolved in toluene and then the separated solvent was evaporated to afford the base as a pale yellow oil. The oil was dissolved in methanol (1575 ml) and treated with N-acetyl-L-leucine (47.5 g). The solution was treated with diethyl ether (274 ml) and (S)-tetrahydropapaverine N-acetyl-L-leucinate (35.5 g) gradually crystallised out. After the crystals had been filtered off the method liquors were evaporated to low bulk to give a solid (100 g), which was then recrystallised from boiling acetone (50 volumes). Upon cooling crystals (74 g, 83% (R)-diastereoisomer, 17% (S)-diastereoisiomer) appeared which were filtered off. The solid was recrystallised once more from boiling acetone (50 volumes) to give 58.7 g of (R)-tetrahydropapaverine N-acetyl-L-leucinate (97% (R)-isomer, 3% (S)-isomer).

c)
(1R,1'R)-2,2'-(3,11-Dioxo-4,10-dioxatridecamethylene)-bis-( 1,2,3,4-tetrahydro-6,7-dimethoxy-1-veratrylisoquinoline)dioxalate (R)-1,2,3,4-Tetrahydropapaverine N-acetyl leucinate (58.7 g) was dissolved in water and treated with aqueous ammonia. The precipitated base was extracted into toluene (600 mls) and, after solvent evaporation, was obtained as an oil (39.0 g). The (R)- 1,2,34-tetrahydropapaverine base was heated with 1,5-penta-methylene diacrylate (10.7 g) and glacial acetic acid (3.0 mls) at 70° C. for 4 hours. The reaction mixture was dissolved in toluene (400 ml) and stirred with silica gel 60 (Merck, column chromatography grade, 70–230 mesh), filtered and evaporated to give a yellow oil. The product was dissolved in acetone (600 ml), treated with oxalic acid (9.3 g) and the dioxalate salt of (1R,1'R)-2,2'-(3,11-dioxo,4,10-dioxatridecamethylene)-bis-(1,2,3,4-tetrahydro- 6,7-dimethoxy-1-veratrylisoquinoline) precipitated as a white solid (54.2 g, 99% yield), m.p. 125° C., h.p.l.c. –97.8%.

d)
(1R,1'R-2,2'-(3,11-Dioxo-4,10-dioxatridecamethylene)-bis-( 1,2,3,4-tetrahydro-6,7-dimethoxy-2-methyl-1-veratrylisoquinolinium)benzenesulphonate ((1R,1'R) Atracurium besylate)

(1R,1'R)-2,2'-(3,11-Dioxo-4,10-dioxatridecamethylene)-bis-(1,2,3,4-tetrahydro- 6,7-dimethoxy-1-veratrylisoquinoline)dioxalate (54.0 g) was dissolved in water (1.6 liters) and treated with sodium carbonate to bring the pH to 7.0. The precipitated base was extracted into toluene (600 mls) and the solvent was then evaporated to give a very viscous yellow oil (42.7 g). The oil was treated with methyl benzenesulphonate (75 mls) at ambient temperature overnight. The product, (1R,1'R)-2,2'-(3,11-dioxo- 4,10-dioxatridecamethylene)-bis-(1,2,3,4-tetrahydro-6,7-dimethoxy- 2-methyl-1-veratrylisoquinolinium)benzenesulphonate was isolated by partitioning between water and toluene. The aqueous phase was further washed with two aliquots of toluene and then subjected to lyophilisation. The product (49.7 g 80% yield) was obtained as a pale yellow solid.

The product is a mixture of (1R,1'R) atracurium besylate isomers, namely, 1R-cis-1'R-cis,1R-cis,1R-trans and 1R-trans,1'R-trans in a ratio of 58:34:6 respectively.

e) 1R-cis,1'R-cis-2,2'-(3,11-Dioxo-4,10-dioxatridecamethylene)-bis-( 1,2,3,4-tetrahydro-6,7-dimethoxy-2-methyl-1-veratrylisoquinolinium)methanesulphonate ((1R-cis, 1'R-cis-Atracurium mesylate)

A mixture of (1R,1'R)-atracurium besylate isomer (10 g) obtained in stage d) was dissolved in dichloromethane (50 mls) and was pumped onto an axially compressed 500 mm×50 mm chromatography column packed with 520 g of 20–45 micron irregular silica, and the methanesulphonic acid (80:20:0.5). Fractions of column eluate were collected, and the fractions containing the required 1R-cis,1'R-cis isomer were combined and washed with 10% brine. The dichloromethane solution was evaporated to dryness, the residual colourless oil was dissolved in water and the pH of the solution was adjusted to 4.0 with methanesulphonic acid. The aqueous solution was lyophilised to give the title compound (5 g) as a white solid which was identified as being substantially free from other geometrical and optical isomers of the compound, namely being in admixture with less than 5% w/w of such isomers, particularly less than 3% w/w of the corresponding 1R-cis,1'S-trans isomer and less than 0.3% w/w of the corresponding 1R-cis,1'R-trans isomer.

EXAMPLE 2

1R-cis,1'R-cis-2,2'-(3,11-Dioxo-4,10-dioxatridecylene)-bis-( 1,2,3,4-tetrahydro-6,7-dimethoxy-2-methyl-veratrylisoquinolinium)benzenesulphonate ((1R-cis,1'R-cis-Atracurium besylate)

Stages a), b), c) and d) of Example 1 were repeated. The product obtained in stage d) was either isolated as described or chromatographed as described below.

(i) A mixture of (1R,1'R)-atracurium besylate isomers (1.5 g of the isomers isolated in stage d) or 3.5 g of the reaction mixture from stage d)) was dissolved in dichloromethane (10 mls) and was pumped onto an axially compressed 300 mm×25 mm chromatography column packed with 80 g of 10 micron spherical silica, and the column was eluted with a mixture of dichloromethane, methanol and benzenesulphonic acid 4000:500:0.25. Fractions of column eluate were collected, and the fractions containing the required 1R-cis, 1'R-cis isomer were combined and washed with 10% brine or water. The dichloromethane solution was evaporated to dryness, the residual colourless oil or semi-solid was dissolved in water and the pH of the soltuion was adjusted to about 4.0 with an aqueous solution of benzenesulphonic acid. The aqueous solution was lyophilised to give the title compound (0.5 g) as a white solid which was identified as being substantially free from other geometrical and optical isomers of the compound, namely being in admixture with less than 5% w/w of such isomers, particularly less than 3% w/w of the corresponding 1R-cis,1'S-trans isomer and less than 0.3% w/w of the corresponding 1R-cis,1'R-trans isomer. The product was analysed by $^1$H NMR (CDCl$_3$) as follows: δ 1.52(m,7CH$_2$-trideca), 1.63(m, 6CH$_2$-trideca,8CH$_2$-trideca), 2.84 (m, ½-4CH$_2$,½-CH$_2$-veratryl), 3.15(m,½-4CH$_2$), 3.22 (s,NCH$_3$), 3.26 (m,2CH$_2$-trideca,12-CH$_2$-trideca), 3.34(s,OCH$_3$), 3.47(m,½-3CH$_2$, ½-CH$_2$-veratryl), 3.58 (s,OCH$_3$), 3.73(2s,OCH$_3$,OCH$_3$), 3.84 (m,½-3CH$_2$), 3.95–4.24 (m, 5CH$_2$-trideca, 9CH$_2$-trideca, 1CH$_2$-trideca, 13CH$_2$-trideca), 4.86 (dd,J=3,8Hz,1H), 5.87(s,8), 6.36(dd,J=8, 2Hz,6H-veratryl), 6.42 (d,J=2Hz,2H-veratryl), 6.48(s,5H), 6.59(d, J=8Hz,5H-veratryl), 7.24(m,meta & para besylate), 7.78(m,ortho besylate).

(ii) A mixture of (1R,1'R)-Atracurium besylate isomers (40 g) was dissolved in dichloromethane (200 ml) and was injected onto an axially compressed 500 mm×100 mm chromatography column packed with 2400 g of 20–45 micron irregular silica, and the column was eluted with a mixture of dichloromethane, methanol and benzenesulphonic acid (4000:500:0.5). Fractions of column eluate were collected and the fractions containing the required 1R-cis,1'R-cis isomer were combined, washed with water to remove methanol and excess benzenesulphonic acid and the resultant dichloromethane solution was evaporated to dryness to give a foamy solid residue. The residue was dissolved in water, the pH of the solution was adjusted to 3.5 to 4.0 with benzenesulphonic acid and the aqueous solution was lyophilised to give (1R-cis,1'R-cis)-Atracurium besylate (15g). Four batches of the 1R cis,1'R-cis isomer produced in this manner were assayed by analytical hplc using a "Partisil" 5μ support and an acetonitrile, water, phosphoric acid; 900:100:10 mobile phase. The flow rate was 2 ml. $\text{min}^{-1}$ using a UV detector preset at 280 nm. The four batches had an isomeric purity of 98.8, 99.5, 99.2 and 99.2% respectively.

(iii) The procedure described in Example 2(ii) was repeated in essentially the same manner except that the column was packed with 2.2 kg of 10 micron spherical silica and the mobile phase was dichloromethane: methanol: benzenesulphonic acid 8500:1500:2.

EXAMPLE 3

Stability of Atracurium under aqueous conditions

The stability of Atracurium in aqueous acid solutions (as would result if an aqueous mobile phase such as those published were used preparatively) was measured. The results are as follows:

| pH | 1.2 | 1.3 | 1.5 | 1.8 | 1.9 | 2.0 |
|---|---|---|---|---|---|---|
| Assay (% after 20 hrs. at 50° C.) | Nil | 7 | 29 | 59 | 69 | 79 |

The aqueous mobile phase published would have pH's in (or more likely lower than) the range give here.

The following Examples illustrate pharmaceutical formulations according to the invention in which the "Active Ingredient" is the 1R-cis, 1'R-cis-atracurium besylate salt according to the invention.

EXAMPLE 4

Unit dose injection solution

| Active Ingredient | 50 mg |
|---|---|
| Benzenesulphonic Acid q.s. to pH | 3 to 4 |
| Water for Injections to make | 5 ml |

Active Ingredient is dissolved in the Water for Injections and the pH of the resulting solution is adjusted as necessary with the acid. The solutions is sterilised by filtration and filled into sterile 5 ml ampoules.

EXAMPLE 5

Multidose injection solution

| Active Ingredient | 100 mg |
|---|---|
| Benzenesulphonic Acid q.s. to pH | 3 to 4 |
| Benzyl Alcohol | 90 mg |
| Water for Injections to make | 10 ml |

Active ingredient and benzyl alcohol are dissolved in the Water for Injections and the pH of the resulting solution is adjusted as necessary with the acid. The solution is sterilised by filtration and filled into sterile 10 ml ampoules.

EXAMPLE 6

Freeze-dried injection solution

| Active Ingredient | 50 mg |
|---|---|
| Benzenesulphonic Acid q.s. to pH | 3 to 4 |
| Mannitol | 62.5 mg |
| Water for Injections to make | 2.5 ml |

The Active Ingredient and manitol are dissolved in the Water for Injections and the pH of the solution is adjusted as necessary with the acid. The solution is sterilised by filtration and filled into sterile vials and freeze-dried.

EXAMPLE 7

Unit dose injection solution

| Active ingredient | 25 mg |
|---|---|
| Benzenesulphonic Acid q.s. to pH | 3 to 4 |
| Water for Injections to make | 5 ml |

Active Ingredient is dissolved in the Water for Injections and the pH of the resulting solution is adjusted as necessary with the acid. The solution is sterilised by filtration and filled into sterile 5 ml ampoules.

We claim:

1. A physiologically acceptable 1R-cis,1'R-cis-2,2'-(3,11-dioxo- 4,10-dioxatridecamethylene)-bis-(1,2,3,4-tetrahydro-6,7-dimethoxy- 2-methyl-1-veratrylisoquinolinium salt being substantially free of other geometric or optical isomers thereof, the amount of said other geometric or optical isomers thereof being less than 8% w/w based on the combined weight of said physiologically acceptable salt and any of said geometric or optical isomers.

2. The salt of claim 1 in which said other geometric or optical isomers thereof is less than 5% w/w.

3. The salt of claim 1 in which said other geometric or optical isomers thereof is less than 2% w/w.

4. A physiologically acceptable 1R-cis,1'R-cis-2,2'-(3,11-dioxo- 4,10-dioxatridecamethylene)-1,2,3,4-tetrahydro-6,7-dimethoxy- 2-methyl-1-veratrylisoquinolinium besylate salt being substantially free of other geometric or optical isomers being less than 8% w/w based on the combined weight of said besylate salt and any of said geometric or optical isomers thereof.

5. The salt of claim 1 in which said other geometric or optical isomers thereof is less than 5% w/w.

6. The salt of claim 1 in which said other geometric or optical isomers thereof is less than 2% w/w.

7. A physiologically acceptable 1R-cis,1'-R-cis-2,2'-(3, 11-dioxo- 4,10-dioxatridecamethylene)-bis-(1,2,3,4-tetrahydro-6,7-dimethoxy- 2-methyl-1-veratrylisoquinolinium mesylate salt being substantially free of other geometric or optical isomers thereof the amount of, said other geometric or optical isomers being less than 8% w/w based on the combined weight of said mesylate salt and any of said geometric or optical isomers thereof.

8. The salt of claim 7 in which said other geometric or optical isomers thereof is less than 5% w/w.

9. The salt of claim 7 in which said other geometric or optical isomers thereof is less than 2% w/w.

10. A pharmaceutically composition comprising the physiologically acceptable salt of claim 1, 2 or 3 in combination with a pharmaceutically acceptable therefor.

11. A pharmaceutically composition comprising the besylate salt of claim 4, 5 or 6 in combination with a pharmaceutical acceptable carrier therefor.

12. A pharmaceutical composition comprising the mesylate salt of claim 7, 8 or 9 in combination with a pharmaceutically acceptable carrier therefor.

13. A method of producing neuromuscular blockage in an animal which comprises administering by injection or infusion to said animal an effective neuromuscular blockade amount of a pharmacologically acceptable liquid containing a physiologically acceptable 1R-cis,1'R-cis-2,2'-(3,11-dioxo- 4,10-dioxatridecamethylene)-bis-(1,2,3,4-tetrahydro-6,7-dimethoxy- 2-methyl-1-veratrylisoquinolinium salt being substantially free of other geometric or optical isomers thereof, the amount of said other geometric or optical isomers thereof being less than 8% w/w based on the combined weight of said physiologically acceptable salt and any of said geometric or optical isomers.

14. The method of claim 11 in which said other geometric or optical isomers thereof is less than 5% w/w.

15. The method of claim 11 in which said other geometric or optical isomers thereof is less than 2% w/w.

16. The method of claim 13, 14 or 15 in which the pharmacologically acceptable salt is the mesylate salt.

17. The method of claim 13 in which the pharmacologically acceptable salt is the besylate salt.

18. The method of claim 14 in which pharmacologically acceptable salt is the besylate salt.

19. The method of claim 15 in which the pharmacologically acceptable salt is the besylate salt.

20. The method of claim 13, 14, 15, 16, 17, 18 or 19 in which the animal is a human.

21. The salt of claim 1, 2, 3, 4, 5, 6, 7, 8 or 9 in solid form.

22. The method of claim 17 in which the animal is a human.

23. The method of claim 18 in which the animal is a human.

24. The method of claim 19 in which the animal is a human.

* * * * *